United States Patent
Volpe et al.

(10) Patent No.: US 9,848,826 B2
(45) Date of Patent: *Dec. 26, 2017

(54) WEARABLE MONITORING AND TREATMENT DEVICE

(71) Applicant: ZOLL MEDICAL CORPORATION, Chelmsford, MA (US)

(72) Inventors: Shane S. Volpe, Saltsburg, PA (US); Thomas E. Kaib, North Huntingdon, PA (US)

(73) Assignee: ZOLL MEDICAL CORPORATION, Chelmsford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/630,920

(22) Filed: Feb. 25, 2015

(65) Prior Publication Data

US 2015/0164427 A1 Jun. 18, 2015

Related U.S. Application Data

(63) Continuation of application No. 14/161,017, filed on Jan. 22, 2014, now Pat. No. 9,131,901, which is a (Continued)

(51) Int. Cl.
*A61B 5/00* (2006.01)
*A61N 1/39* (2006.01)
(Continued)

(52) U.S. Cl.
CPC ........ *A61B 5/7221* (2013.01); *A41D 13/1281* (2013.01); *A61B 5/0205* (2013.01);
(Continued)

(58) Field of Classification Search
CPC ... A61B 5/7221; A61B 5/6802–5/6831; A61B 5/6843–5/6844
See application file for complete search history.

(56) References Cited

U.S. PATENT DOCUMENTS

| | | | |
|---|---|---|---|
| 4,094,310 | A | 6/1978 | McEachern et al. |
| 4,632,122 | A | 12/1986 | Johansson et al. |

(Continued)

FOREIGN PATENT DOCUMENTS

| | | |
|---|---|---|
| CN | 201657785 U | 12/2010 |
| EP | 0295497 B1 | 9/1993 |

(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/full/166/1/111.

(Continued)

*Primary Examiner* — Michael Kahelin
(74) *Attorney, Agent, or Firm* — Lando & Anastasi, LLP

(57) ABSTRACT

A wearable medical device is provided. The wearable medical device includes a garment that includes a sensing electrode, at least one of an inductive element and a capacitive element included in at least part of the garment, and a controller. The controller may be configured to determine a confidence level of information received from the sensing electrode based on at least one of an inductance of the inductive element and a capacitance of the capacitive element.

14 Claims, 5 Drawing Sheets

Related U.S. Application Data continuation of application No. 13/598,380, filed on Aug. 29, 2012, now Pat. No. 8,644,925.

(60) Provisional application No. 61/679,143, filed on Aug. 3, 2012, provisional application No. 61/530,261, filed on Sep. 1, 2011.

(51) Int. Cl.
*G01R 27/26* (2006.01)
*A41D 13/12* (2006.01)
*A61N 1/04* (2006.01)
*A61B 5/053* (2006.01)
*A61B 5/113* (2006.01)
*A61B 5/0205* (2006.01)
*A61B 5/0452* (2006.01)
*A61B 5/024* (2006.01)

(52) U.S. Cl.
CPC ............ *A61B 5/0452* (2013.01); *A61B 5/053* (2013.01); *A61B 5/1135* (2013.01); *A61B 5/6804* (2013.01); *A61B 5/6844* (2013.01); *A61B 5/742* (2013.01); *A61B 5/7455* (2013.01); *A61N 1/046* (2013.01); *A61N 1/0484* (2013.01); *A61N 1/3925* (2013.01); *A61N 1/3968* (2013.01); *A61N 1/3975* (2013.01); *A61N 1/3987* (2013.01); *G01R 27/2611* (2013.01); *A61B 5/02438* (2013.01); *A61B 5/6805* (2013.01); *A61N 1/3931* (2013.01)

(56) References Cited

U.S. PATENT DOCUMENTS

| | | | |
|---|---|---|---|
| 4,928,690 A | 5/1990 | Heilman et al. | |
| 4,978,926 A | 12/1990 | Zerod et al. | |
| 5,062,834 A | 11/1991 | Gross et al. | |
| 5,078,134 A | 1/1992 | Heilman et al. | |
| 5,348,008 A | 9/1994 | Bornn et al. | |
| 5,365,932 A | 11/1994 | Greenhut | |
| 5,472,453 A | 12/1995 | Alt | |
| 5,662,689 A | 9/1997 | Elsberry et al. | |
| 5,718,242 A | 2/1998 | McClure et al. | |
| 5,738,102 A | 4/1998 | Lemelson | |
| 5,741,306 A | 4/1998 | Glegyak et al. | |
| 5,758,443 A | 6/1998 | Pedrazzini | |
| 5,792,190 A | 8/1998 | Olson et al. | |
| 5,887,978 A | 3/1999 | Lunghofer et al. | |
| 5,929,601 A | 7/1999 | Kaib et al. | |
| 5,944,669 A | 8/1999 | Kaib | |
| 6,016,445 A | 1/2000 | Baura | |
| 6,045,503 A | 4/2000 | Grabner et al. | |
| 6,047,203 A | 4/2000 | Sackner et al. | |
| 6,065,154 A | 5/2000 | Hulings et al. | |
| 6,097,982 A | 8/2000 | Glegyak et al. | |
| 6,097,987 A | 8/2000 | Milani | |
| 6,169,397 B1 | 1/2001 | Steinbach et al. | |
| 6,253,099 B1 | 6/2001 | Oskin et al. | |
| 6,280,461 B1 | 8/2001 | Glegyak et al. | |
| 6,390,996 B1 | 5/2002 | Halperin et al. | |
| 6,406,426 B1 | 6/2002 | Reuss et al. | |
| 6,681,003 B2 | 1/2004 | Linder et al. | |
| 6,690,969 B2 | 2/2004 | Bystrom et al. | |
| 6,804,554 B2 | 10/2004 | Ujhelyi et al. | |
| 6,827,695 B2 | 12/2004 | Palazzolo et al. | |
| 6,908,437 B2 | 6/2005 | Bardy | |
| 6,961,612 B2 | 11/2005 | Elghazzawi et al. | |
| 6,990,373 B2 | 1/2006 | Jayne et al. | |
| 7,149,579 B1 | 12/2006 | Koh et al. | |
| 7,220,235 B2 | 5/2007 | Geheb et al. | |
| 7,340,296 B2 | 3/2008 | Stahmann et al. | |
| 7,453,354 B2 | 11/2008 | Reiter et al. | |
| 7,488,293 B2 | 2/2009 | Marcovecchio et al. | |
| 7,712,373 B2 | 5/2010 | Nagle et al. | |
| 7,831,303 B2 | 11/2010 | Rueter et al. | |
| 7,974,689 B2 | 7/2011 | Volpe et al. | |
| 8,121,683 B2 | 2/2012 | Bucher et al. | |
| 8,140,154 B2 | 3/2012 | Donnelly et al. | |
| 8,271,082 B2 | 9/2012 | Donnelly et al. | |
| 2003/0004547 A1 | 1/2003 | Owen et al. | |
| 2003/0095648 A1 | 5/2003 | Kaib et al. | |
| 2003/0149462 A1 | 8/2003 | White et al. | |
| 2003/0158593 A1 | 8/2003 | Heilman et al. | |
| 2003/0174049 A1 | 9/2003 | Beigel et al. | |
| 2003/0195567 A1 | 10/2003 | Jayne et al. | |
| 2003/0212311 A1 | 11/2003 | Nova et al. | |
| 2004/0049233 A1 | 3/2004 | Edwards | |
| 2005/0049515 A1 | 3/2005 | Misczynski et al. | |
| 2005/0131465 A1 | 6/2005 | Freeman et al. | |
| 2006/0036292 A1 | 2/2006 | Smith et al. | |
| 2006/0085049 A1 | 4/2006 | Cory et al. | |
| 2006/0149146 A1* | 7/2006 | Schmidt ............... A61B 5/0006 600/372 |
| 2006/0178706 A1 | 8/2006 | Lisogurski et al. | |
| 2006/0270952 A1 | 11/2006 | Freeman et al. | |
| 2007/0118056 A1 | 5/2007 | Wang et al. | |
| 2007/0161913 A1 | 7/2007 | Farrell et al. | |
| 2007/0169364 A1 | 7/2007 | Townsend et al. | |
| 2007/0239220 A1 | 10/2007 | Greenhut et al. | |
| 2007/0265671 A1 | 11/2007 | Roberts et al. | |
| 2008/0004536 A1 | 1/2008 | Baxi et al. | |
| 2008/0030656 A1 | 2/2008 | Watson et al. | |
| 2008/0033495 A1 | 2/2008 | Kumar | |
| 2008/0045815 A1 | 2/2008 | Derchak et al. | |
| 2008/0046015 A1 | 2/2008 | Freeman et al. | |
| 2008/0058884 A1 | 3/2008 | Matos | |
| 2008/0167535 A1 | 7/2008 | Stivoric et al. | |
| 2008/0249591 A1 | 10/2008 | Gaw et al. | |
| 2008/0306560 A1 | 12/2008 | Macho et al. | |
| 2009/0018428 A1 | 1/2009 | Dias et al. | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076344 A1 | 3/2009 | Libbus et al. | |
| 2009/0076345 A1 | 3/2009 | Manicka et al. | |
| 2009/0076346 A1 | 3/2009 | James et al. | |
| 2009/0076348 A1 | 3/2009 | Manicka et al. | |
| 2009/0076349 A1 | 3/2009 | Libbus et al. | |
| 2009/0076350 A1 | 3/2009 | Bly et al. | |
| 2009/0076363 A1 | 3/2009 | Bly et al. | |
| 2009/0076364 A1 | 3/2009 | Libbus et al. | |
| 2009/0076397 A1 | 3/2009 | Libbus et al. | |
| 2009/0076405 A1 | 3/2009 | Amurthur et al. | |
| 2009/0076410 A1 | 3/2009 | Libbus et al. | |
| 2009/0076559 A1 | 3/2009 | Libbus et al. | |
| 2009/0088652 A1 | 4/2009 | Tremblay | |
| 2009/0093687 A1 | 4/2009 | Telfort et al. | |
| 2009/0138059 A1 | 5/2009 | Ouwerkerk | |
| 2009/0234410 A1 | 9/2009 | Libbus et al. | |
| 2009/0264792 A1 | 10/2009 | Mazar | |
| 2009/0275848 A1 | 11/2009 | Brockway et al. | |
| 2009/0281394 A1 | 11/2009 | Russell et al. | |
| 2009/0287120 A1 | 11/2009 | Ferren et al. | |
| 2009/0292194 A1 | 11/2009 | Libbus et al. | |
| 2010/0056881 A1 | 3/2010 | Libbus et al. | |
| 2010/0069735 A1 | 3/2010 | Berkner | |
| 2010/0076513 A1 | 3/2010 | Warren et al. | |
| 2010/0234716 A1 | 9/2010 | Engel | |
| 2010/0295674 A1 | 11/2010 | Hsieh et al. | |
| 2010/0298899 A1 | 11/2010 | Donnelly et al. | |
| 2011/0015533 A1 | 1/2011 | Cox et al. | |
| 2011/0034811 A1 | 2/2011 | Naujokat et al. | |
| 2011/0087300 A1 | 4/2011 | Van Den Eerenbeemd et al. | |
| 2011/0288604 A1 | 11/2011 | Kaib et al. | |
| 2011/0288605 A1 | 11/2011 | Kaib et al. | |
| 2012/0011382 A1 | 1/2012 | Volpe et al. | |
| 2012/0112903 A1 | 5/2012 | Kaib et al. | |

(56) References Cited

U.S. PATENT DOCUMENTS

2012/0146797 A1    6/2012   Oskin et al.
2012/0150008 A1    6/2012   Kaib et al.
2012/0158075 A1    6/2012   Kaib et al.

FOREIGN PATENT DOCUMENTS

| EP | 0335356 B1 | 3/1996 |
|---|---|---|
| EP | 1455640 B1 | 1/2008 |
| EP | 1720446 B1 | 7/2010 |
| JP | 5115450 A | 5/1993 |
| WO | 0002484 A1 | 1/2000 |
| WO | 2004054656 A1 | 7/2004 |
| WO | 2004078259 A1 | 9/2004 |
| WO | 2006050325 A2 | 5/2006 |
| WO | 2010025432 A1 | 3/2010 |
| WO | 2010077997 A2 | 7/2010 |
| WO | 2010131267 A1 | 11/2010 |

OTHER PUBLICATIONS

DeBock, et al., "Captopril treatment of chronic heart failure in the very old," J. Gerontol. (1994) 49: M148-M152.
International Search Report and Written Opinion from corresponding PCT application PCT/US2012/052896 dated Nov. 16, 2012.
O'Keeffe et al., "Reproducability and responsiveness of quality of life assessment and six minute walk test in elderly heart failure patients," Heart (1998) 80: 377-382.
Extended Search Report from corresponding European application 12826705.1, dated Mar. 20, 2015.

\* cited by examiner

WEARABLE MONITORING AND TREATMENT DEVICE

CROSS REFERENCE TO RELATED APPLICATIONS

This application claims priority under 35 U.S.C. §120 to U.S. application Ser. No. 14/161,017, (now U.S. Pat. No. 9,131,901) titled "WEARABLE MONITORING AND TREATMENT DEVICE", filed Jan. 22, 2014, which claims priority under 35 U.S.C. §120 to U.S. application Ser. No. 13/598,380, (now U.S. Pat. No. 8,644,925) titled "WEARABLE MONITORING AND TREATMENT DEVICE", filed Aug. 29, 2012, which claims priority under 35 U.S.C. §119(e) to U.S. Provisional Application Ser. No. 61/530,261 titled "WEARABLE MONITORING AND TREATMENT DEVICE," filed Sep. 1, 2011, and to U.S. Provisional Application Ser. No. 61/679,143 titled "WEARABLE MONITORING AND TREATMENT DEVICE," filed Aug. 3, 2012, each of which is incorporated herein by reference in its entirety.

BACKGROUND OF THE INVENTION

1. Field of the Invention

At least one embodiment of the present invention relates generally to a wearable therapeutic device, and more specifically, to a wearable therapeutic device configured to monitor or treat a subject.

2. Discussion of Related Art

Cardiac arrest and other health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival. Health care professionals also attempt to detect and prevent conditions conducive to cardiac ailments by treating patients with drugs or by suggesting lifestyle changes. These efforts are expensive and have a limited success rate, and cardiac arrest, among other conditions, continues to claim the lives of victims.

SUMMARY OF THE INVENTION

Aspects and embodiments of the present invention are directed to a wearable therapeutic device that is configured to be worn by a subject. Electrodes sense information about the subject's health, and can apply treatment to the subject. At least one inductive or capacitive element is included in a portion of the therapeutic device. Characteristics of the inductive or capacitive element, such as its radius or shape, change when the wearable therapeutic device expands, stretches, or otherwise changes shape, which changes the inductance of the inductive element or the capacitance of the capacitive element. Based at least in part on changes in the inductance or the capacitance as the wearable therapeutic device changes shape, the wearable therapeutic device can provide notifications to the subject regarding arrhythmias, cardiac events, the condition of the wearable therapeutic device, and the positioning of electrodes or other wearable therapeutic device components relative to the subject.

At least one aspect is directed to a wearable therapeutic device. The wearable therapeutic device includes a garment that is configured to include a sensing electrode. At least one of an inductive element and a capacitive element is included in at least part of the garment, and a controller is configured to determine a confidence level of information received from the sensing electrode based on at least one of an inductance of the inductive element and a capacitance of the capacitive element.

At least one other aspect is directed to a method of facilitating care of a subject. The method provides a wearable therapeutic device configured to include a sensing electrode, and receives, from the sensing electrode, information about the subject. The method also determines inductance of an inductive element or capacitance of a capacitive element included in the wearable therapeutic device, and determines a confidence level of the information about the subject based on the inductance or the capacitance.

At least one other aspect is directed to a non-transitory computer readable medium having stored thereon sequences of instruction. The instructions include instructions that will cause a processor to receive, from a sensing electrode of a wearable therapeutic device, information about a subject, and to determine inductance of an inductive element or capacitance of a capacitive element included in the wearable therapeutic device. The instructions also cause the processor to determine a confidence level of the information about the subject based on the inductance or the capacitance.

In some embodiments, the wearable therapeutic device includes an alarm module coupled with the controller and configured to provide a notification to a subject based on the confidence level. In one embodiment, the controller determines at least one of the inductance of the inductive element or the capacitance of the capacitive element. Based on the confidence level, in some embodiments a notification to the subject is provided regarding at least one of a diagnosis and information about the wearable therapeutic device.

In various embodiments, a therapy electrode is included in the garment. The controller can determine information regarding positioning of the therapy electrode or the sensing electrode based on the inductance of the inductive element or the capacitance of the capacitive element. A defibrillator is coupled to the therapy electrode and together with the therapy electrode can apply treatment to the subject, based on the confidence level of the information received from the sensing electrode. The controller can identify, based on the inductance or the capacitance, an expansion of the garment, and can determine, based on the expansion, that positioning of at least one of the sensing electrode and the therapy electrode is outside a tolerance range. In one embodiment, the controller can withhold treatment of the subject based on the positioning of at least one of the sensing electrode and the therapy electrode. The controller can determine, based on the expansion of the garment, respiratory function of the subject. In one embodiment, the alarm module can provide instructions to the subject regarding positioning of the sensing electrode or the therapy electrode based on the expansion of the garment. The controller can determine a second inductance value of the inductive element and can determine the confidence level based on a differential between the first inductance value and the second inductance value. The controller can also determine a second capacitance value of the capacitive element and can determine the confidence level based on a differential between the first capacitance value and the second capacitance value.

In some embodiments, a belt or a strap is configured to include at least one of the inductive element and the capacitive element, and at least one of the sensing electrode, the controller, the alarm module, a therapy electrode, and a defibrillator. In on embodiment in which the belt or strap includes an inductive element, the belt can include a core, wherein the inductive element is coiled around the core. The notification can indicate that the garment is properly positioned about the subject, too loose about the subject, too tight about the subject, soiled, or expired.

In some embodiments, the information received from the sensing electrode includes electrocardiograph information of the subject, and the confidence level can be determined based on the expansion of the garment and the electrocardiograph information of the subject. An arrhythmic cardiac event can be identified based on the confidence level, positioning of the therapy electrode can be verified, and the therapy electrode can be instructed to apply treatment to the subject. The controller can determine the confidence level based on the electrocardiograph information of the subject. The controller can also determine an absence of an arrhythmic cardiac event based on the inductance of the inductive element or the capacitance of the capacitive element and the electrocardiograph information of the subject.

In some embodiments, the wearable therapeutic device includes a therapy electrode and a defibrillator. The positioning of the sensing electrode or the therapy electrode can be verified based on the inductance of the inductive element or the capacitance of the capacitive element. Treatment can be applied to the subject using the therapy electrode and the defibrillator. The inductive element or the capacitive element can be included in a belt of the wearable therapeutic device, and an expansion of a circumference of the belt can be identified based on the inductance of the inductive element or the capacitance of the capacitive element. The confidence level of the information about the subject can be determined based on the expansion of the circumference of the belt. In one embodiment, the inductive element or the capacitive element is in a garment of the wearable therapeutic device, and an expansion of the garment can be identified based on the inductance of the inductive element or the capacitance of the capacitive element. Instructions can be provided to the subject regarding positioning of the sensing electrode or the therapy electrode based on the expansion of the garment.

In various embodiments, the diagnosis includes a diagnosis of an arrhythmic cardiac event. Electrocardiograph information of the subject can be sensed, and an expansion of a portion of the wearable therapeutic device that includes at least one of the inductive element and the capacitive element can be identified. The confidence level can be determined based on the expansion of the portion of the wearable therapeutic device and the electrocardiograph information of the subject, and the arrhythmic cardiac event can be identified based on the confidence level. An absence of an arrhythmic cardiac event can also be determined based on the confidence level.

In one embodiment, improper positioning of the sensing electrode or the therapy electrode can be identified based on the expansion. An absence of an arrhythmic cardiac event can be identified based on the improper positioning of the sensing electrode. In one embodiment, treatment of the subject can be withheld based on the improper positioning of the sensing electrode or the therapy electrode.

In some embodiments, instructions to operate the wearable therapeutic device can be provided. In one embodiment, instructions can cause a processor to receive sensed electrocardiograph information of the subject, and identify an expansion of a portion of the wearable therapeutic device that includes the inductive element or the capacitive element. The instructions can cause the processor to determine the confidence level based on the expansion of the portion of the wearable therapeutic device and the electrocardiograph information of the subject, and to identify an arrhythmic cardiac event based on the confidence level. The instructions can cause the processor to control the therapy electrode of the wearable therapeutic device to apply treatment to the subject. In one embodiment, the instructions can cause the processor to determine an absence of an arrhythmic cardiac event based on the confidence level.

Other aspects and embodiments are discussed in detail below. The foregoing information and the following detailed description include illustrative examples of various aspects and embodiments, and are intended to provide an overview or framework for understanding the nature and character of the claimed aspects and embodiments. The drawings provide illustration and a further understanding of the various aspects and embodiments, and are incorporated in and constitute a part of this specification. The drawings, together with the remainder of the specification, serve to describe and explain the claimed aspects and embodiments.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
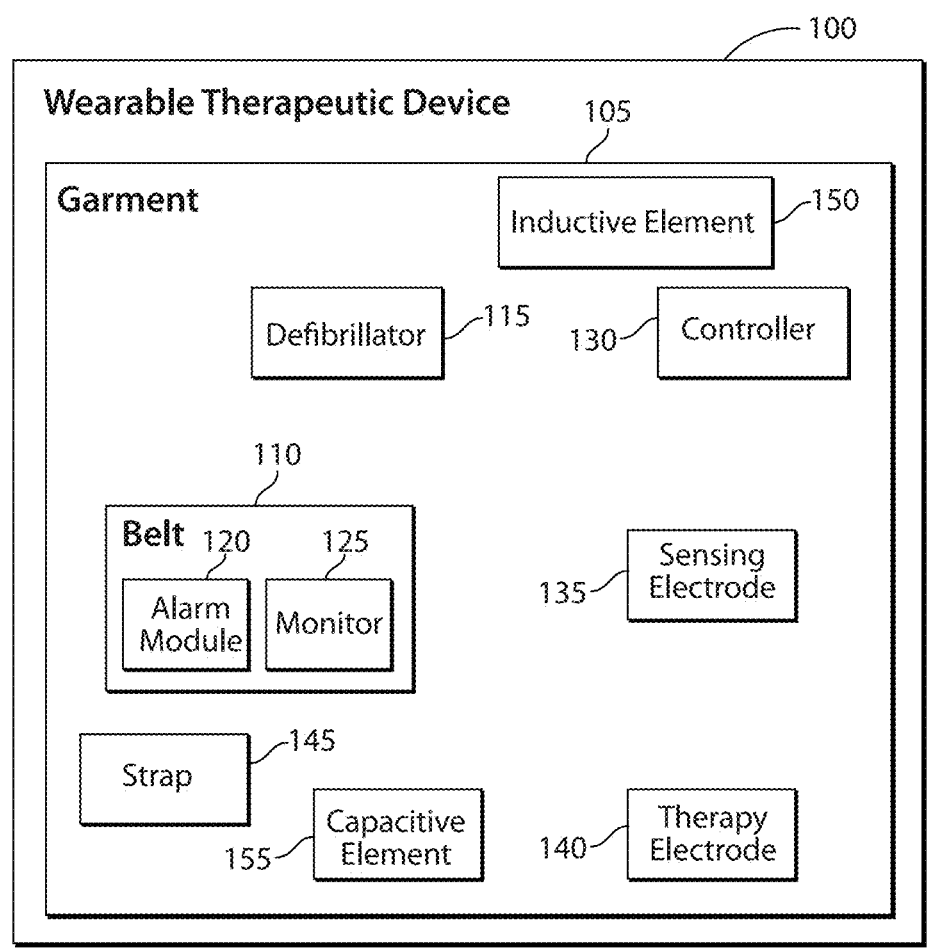
FIG. 1 is a block diagram depicting a wearable therapeutic device in accordance with an embodiment.

The systems and methods described herein are not limited in their application to the details of construction and the arrangement of components set forth in the description or illustrated in the drawings. The systems and methods described herein are capable of other embodiments and of being practiced or of being carried out in various ways. Also, the phraseology and terminology used herein is for the purpose of description and should not be regarded as limiting. The use of "including" "comprising" "having" "containing" "involving" and variations thereof herein, is meant to encompass the items listed thereafter, equivalents thereof, and additional items, as well as alternate embodiments consisting of the items listed thereafter exclusively.

Various aspects and embodiments are directed to a wearable therapeutic device. The wearable therapeutic device includes at least a sensing electrode. An inductive or capacitive element is integrated into the wearable therapeutic device. Inductance of the inductive element or capacitance of the capacitive element varies as these elements change shape, for example due to stretching with use of the wearable therapeutic device. A controller determines the inductance of the inductive element or capacitance of the capacitive element and together with an alarm module or other interface or output, can provide a notification to the subject regarding, for example, the wearable treatment device, a diagnosis, or a treatment regimen.

FIG. 1 is a block diagram of a wearable therapeutic device 100 in accordance with an embodiment. In one embodiment, the wearable therapeutic device 100 can be a wearable cardioverter defibrillator as described in commonly owned U.S. patent application Ser. No. 13/109,079, titled "Wearable Therapeutic Device," filed on May 17, 2011, which is incorporated by reference herein in its entirety.

Wearable therapeutic device 100 can include at least one garment 105 in the shape of a vest or shirt. Garment 105 may also include at least one belt 110. Belt 110 may be worn about a subject's waist, at a higher location about the subject's chest, or at other locations between the subject's waist and shoulders. Components of wearable therapeutic device 100, including garment 105, can be worn under, over, or partially under and partially over a subject's clothes.

In one embodiment, wearable therapeutic device 100 includes at least one of the following elements: garment 105, belt 110, defibrillator 115, alarm module 120, monitor 125, controller 130, sensing electrode 135, therapy electrode 140, strap 145, inductive element 150, and capacitive element 155. In one embodiment, at least one of defibrillator 115, alarm module 120, monitor 125, controller 130, sensing electrode 135, therapy electrode 140, inductive element 150, and capacitive element 155 are included in or attached to belt 110 or strap 145. For example, wearable therapeutic device 100 components can be fitted into open or closed pockets of belt 110 or strap 145, or otherwise attached to these elements via buckles, hook and loop fasteners, holsters, loops, or sleeves that form part of belt 110 or strap 145. These elements may also be integrated into belt 110 or strap 145, and these elements may be a permanent part of belt 110 or strap 145, or releasable from belt 110 or strap 145. Garment 105 may include a series of belts 110 or straps 145, and need not constitute an article of clothing. Wearable therapeutic device 100 may include one, more than one, or all of the above mentioned elements, as well as additional elements such as at least one power supply to provide power to controller 130, defibrillator 115, alarm module 120, monitor 125, sensing electrodes 135, or therapy electrodes 140.

Defibrillator 115 can be included as part of wearable therapeutic device 100. For example, defibrillator 115 can be included in garment 105, attached to strap 145, or disposed in belt 110. In one embodiment, defibrillator 115 is electrically coupled to therapy electrode 140. Defibrillator 115 can be an external defibrillator. Wearable therapeutic device 100 may include at least one receptacle having a conductive fluid encapsulated therein and housed in garment 105. For example, the receptacle can be disposed in belt 110 or strap 145, proximate to at least one of sensing electrode 135 and therapy electrode 140. In one embodiment, electrodes 135 and 140 are dry electrodes. Controller 130 or defibrillator 115 can release the conductive fluid from the receptacles to enhance an electrical connection between sensing electrode 135 or therapy electrode 140 and a subject wearing wearable therapeutic device 100 to, for example, sense electrocardiograph information about the subject or to apply treatment to the subject. The receptacles can be replaced after their conductive fluid has been released, or upon their expiration. When a shock is applied, therapy electrodes 140, the subject's body, and defibrillator 115 form at least part of a current path. One embodiment includes at least one sensing electrode 135, one therapy electrode 140 disposed in front of the subject, e.g., proximate to the subject's chest, and two therapy electrodes 140 disposed in back of the subject, e.g. proximate to the subject's back.

Garment 105 can hold electrodes 135 and 140 in position, for example against the subject's skin around the subject's torso. Clothes or other material may be present between garment 105 and the subject's skin. When positioned against the subject, sensing electrodes 135 can sense electrocardiogram signals used by controller 130 to monitor the subject's cardiac activity. When controller 130 identifies an arrhythmia or other cardiac event, therapy electrodes 140, when positioned against the subject can deliver defibrillating energy to the subject to convert the arrhythmia to a normal sinus rhythm.

In one embodiment, sensing electrodes 135 and therapy electrodes 140 are securely positioned against the subject's body in order for sensing electrodes 135 to sense cardiac, respiratory, or other information about the subject; and for therapy electrodes 140 to apply treatment to the subject. For example, sensing electrode 135 can include electrocardiogram electrodes that directly or indirectly (e.g., via clothes, a conductive protective barrier, or a conductive fluid) contact the subject's skin to sense an electrocardiogram signal with minimal artifacts. Further, therapy electrode 140 can directly or indirectly contact the subject's skin to reduce impedance between therapy electrode 140 and the subject's skin and to efficiently deliver defibrillating energy to the subject, without causing burns, blisters, inflammation, or other damage to the subject's skin. In one embodiment, conductive fluid is released from replaceable receptacles that are disposed in wearable therapeutic device 100 to contact the subject's skin and surfaces of sensing electrode 135 or therapy electrode 140 to reduce impedance and improve the quality of sensed electrocardiogram signals.

In one embodiment, controller 130 includes at least one processor as described in commonly owned U.S. patent application Ser. No. 12/833,096, titled "System and Method for Conserving Power in a Medical Device," filed on Jul. 9, 2010 (hereinafter "the '096 application"), which is incorporated by reference herein in its entirety. The '096 application generally describes a processing architecture configured to conserve energy and which may be used in a wearable therapeutic device, such as a wearable defibrillator. Controller 130 can monitor a subject's condition and control wearable therapeutic device 100 operations. For example, sensing electrode 135 can sense electrical activity of the subject's heart signals, and controller 130 can provide these signals for display as an electrocardiograph on monitor 125. When an arrhythmic event or other form of cardiac distress is detected, controller 130 can instruct alarm module 120 to provide a warning that the subject wearing wearable therapeutic device 100 is in danger of, or is experiencing, for example, cardiac arrest. Where the subject does not respond to the warning, the controller 130 can direct the defibrillator 115 to apply an electric shock to the body of the subject in an effort to restore a normal rhythm. Information concerning the subject's condition, such as the subject's electrocardiogram (ECG), information relating to detected arrhythmic events, information pertaining to any defibrillation shocks applied to the subject, and other information can be stored in memory units associated with controller 130 for analysis by a doctor, rescuer, the subject, or a health care provider.

In one embodiment, the functionality of defibrillator 115 may be performed at least partially in software executed by the at least one processor of the controller 130 in a manner such as described in the '096 application. In other embodiments, the functionality of defibrillator 115 may be implemented in a Field Programmable Gate Array (FPGA), one or more Programmable Logic Devices (PLDs), a Complex PLD (CPLD), a custom Application Specific Integrated Circuit (ASIC), or a dedicated processor operating under the control of the at least one processor of the controller 130. It should be appreciated that other implementations may be used, as the present invention is not limited to any particular implementation.

In one embodiment, alarm module 120 provides an alarm or warning that indicates that the subject will receive an electric shock from defibrillator 115 and at least one therapy electrode 140 when the subject is wearing wearable therapeutic device 100, with therapy electrode 140 disposed proximate to the subject's body. This alarm or warning may be audio, visual, haptic (e.g., vibrating alarm module 120) or combinations thereof. Treatment in the form of an electric shock can be applied to the subject wearing wearable therapeutic device 100 unless the subject takes some action to prevent defibrillator 115 from applying the shock. For example, alarm module 120 or monitor 125 may include an interface having at least one button or touch screen. In this example, the subject can depress a button. This indicates that the subject is conscious. In this example, the shock will not be applied while the subject depresses the button for a sufficient amount of time, or until controller 130 determines that the electrical heart activity of the subject, detected for example by sensing electrode 135, has returned to normal. Continuing with this example, if the subject looses consciousness, the subject will release the buttons and defibrillator 115 can apply a shock via at least one therapy electrode 140.

Alarm module 120 can be part of monitor 125 or a separate element of wearable therapeutic device 100. In one embodiment, alarm module 120 alerts and instructs the subject to take corrective action to reposition sensing electrode 135 or therapy electrode 140. For example, alarm module 120 can instruct the subject to tighten belt 110 to position or reposition sensing electrode 135 or therapy electrode 140. This can reduce, for example, signal interference at sensing electrode 135 by positioning this electrode proximate to the subject's skin, or proximate to a desired portion of the subject's body where a stronger electrocardiogram signal can be sensed. This can also reduce impedance between therapy electrode 140 and the subject, or between a plurality of therapy electrodes 140, allowing for more efficient and effective application of therapy to the subject.

In one embodiment, at least one sensing electrode 135 and at least one therapy electrode 140 are permanent components of wearable therapeutic device 100. Electrodes 135 and 140 can be housed anywhere in garment 105. For example, at least one sensing electrode 135 can be integral to garment 105 and disposed proximate to the subject's chest or abdomen when the subject is wearing wearable therapeutic device 100. At least one therapy electrode 140 can be integral to garment 105 and disposed proximate to the subject's back when the subject is wearing wearable therapeutic device 100. Sensing electrode 135 and therapy electrode 140 may include conductive surfaces such as a metal plate or foil in a generally circular, ovoid, or quadrilateral shape.

In one embodiment, sensing electrode 135 and therapy electrode 140 include conductive thread woven, sewn, or embroidered into wearable treatment device 100. The conductive thread can provide connections between any of electrodes 135 and 140, and a battery powered defibrillator 115. In one embodiment, sensing electrode 135 senses the subject's electrocardiogram signals and provides that signal to defibrillator 115.

The conductive thread that may form at least part of sensing electrode 135 and therapy electrode 140 can have various patterns to achieve proper electrocardiogram sensing and to administer therapy. In one embodiment, sensing electrode 135 or therapy electrode 140 include only conductive stitching. Sensing electrode 135 or therapy electrode 140 may also include conductive stitching that holds a metal foil or other conductive component in place in garment 105, so that sensing electrode 135 or therapy electrode 140 includes both conductive thread and a conductive foil.

The conductive thread can be sewn into garment 105 (e.g., belt 110) in a zigzag pattern that can stretch as part of garment 105. This stretchable conductive thread stitching connects sensing electrode 135 and therapy electrode 140 with controller 130 or other garment 105 components (e.g., defibrillator 115) in the absence of additional wires. In one embodiment, the conductive thread (e.g., conductive wiring) can face toward or away from the subject's skin.

In one embodiment, garment 105 includes breathable fabric, or a material that wicks heat away from the subject's body. This can reduce heat buildup between the subject's skin and sensing electrode 135 or therapy electrode 140. Using conductive thread for electrodes 135 or 140 reduces heat buildup in one embodiment when electrodes 135 or 140 are formed from conductive thread in the absence of any further metallic or conductive foil. In one embodiment, sensing electrode 135 or therapy electrode 140 are made of perforated materials that allow air flow proximate to the subject's skin. This air flow can dry sweat or other fluid from the skin to avoid rashes and other skin problems as a result of heat buildup and irritation.

Garment 105 can be adjusted to snugly fit the subject. For example, portions of garment 105 that include sensing electrode 135 and therapy electrode 140 can be substantially flush against the subject, e.g., electrodes 135 and 140 remain substantially in a fixed position against the subject when the subject is moving about as part of a daily routine, or undertaking moderate physical activity. Clothing may be present between garment 105 and the subject. Where clothing is present between garment 105 and the subject, the clothing preferably includes openings to permit electrodes 135 to directly contact the subject's skin. Alarm module 120 can alert the subject when wearable therapeutic device 100 is not sufficiently tight and snug about the subject. For example, alarm module 120 can notify the subject when the portion of garment 105 that includes sensing electrode 135 or therapy electrode 140 is not flush with or fairly tightly pressed against the patient in a substantially fixed position.

Garment 105 or its components such as belt 110 or strap 145 may expand or stretch with time or repeated use, which can loosen the fit and positioning of sensing electrode 135 and therapy electrode 140 proximate to the subject. Further, the subject's respiration will typically result in periodic expansion of garment 105. Controller 130 can detect this expansion and where appropriate, instruct the subject to reposition sensing electrode 135 or therapy electrode 140, for example by tightening garment 105.

To identify garment 105 stretching, in one embodiment wearable therapeutic device 100 includes at least one inductive element 150. Inductive element 150 includes a metallic or other conductive material, such as a conductive wire or thread that is configured in a coiled pattern (e.g., spring shaped) that includes a plurality of coils (e.g., windings or turns) with a substantially similar radius. In one embodiment, inductive element 150 includes at least one coiled conductive element that acts as an inductor when alternating current is applied to it. In some embodiments, a magnetic core may be disposed within the plurality of coils.

Figure 3A:
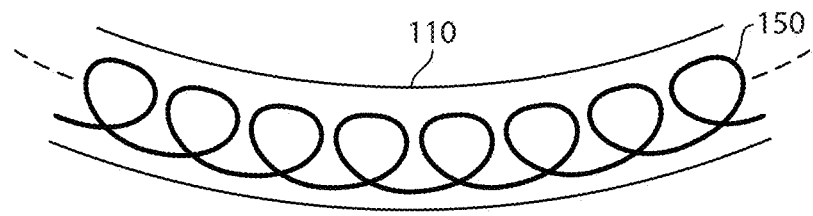
FIG. 3A is a schematic diagram depicting a portion of a wearable therapeutic device that includes an inductive element in an unstretched position in accordance with an embodiment.
Figure 3B:
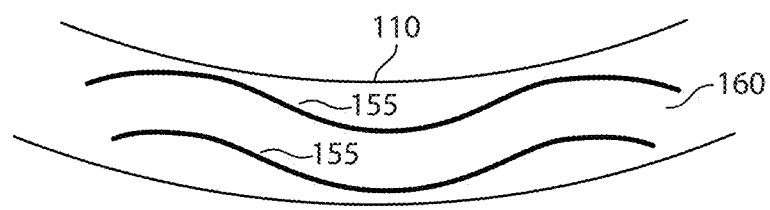
FIG. 3B is a schematic diagram depicting a portion of a wearable therapeutic device that includes a capacitive element in an unstretched position in accordance with an embodiment.
Figure 4A:
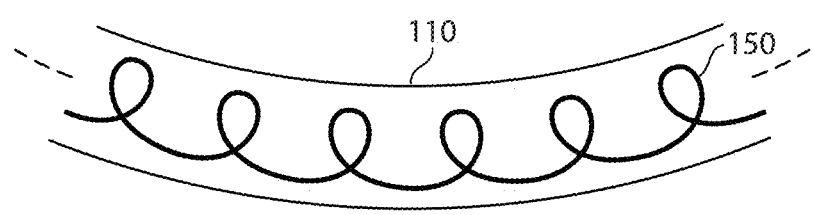
FIG. 4A is a schematic diagram depicting a portion of a wearable therapeutic device that includes an inductive element in a stretched position in accordance with an embodiment.
Figure 4B:
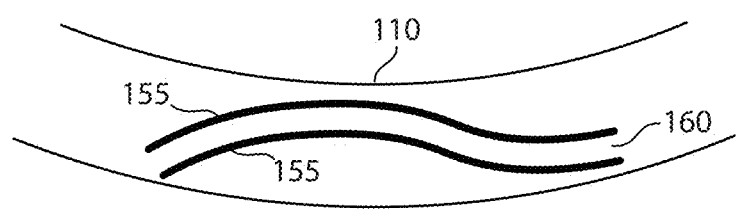
FIG. 4B is a schematic diagram depicting a portion of a wearable therapeutic device that includes a capacitive element in a stretched position in accordance with an embodiment.

In an alternate embodiment, inductive element 150 may be formed from a conductive wire or thread that is configured in a serpentine pattern similar in shape to that shown in FIGS. 3B and 4B that includes a plurality of serpentine turns of similar dimension.

In another embodiment, wearable therapeutic device 100 includes at least one capacitive element 155 to identify garment 105 stretching. In one embodiment, the at least one capacitive element 155 can be formed from a conductive material such as a pair of wires with a round circumference or with at least one flat side, configured in parallel with each other in a serpentine or coiled pattern in garment 105. A space may be present between two capacitive elements 155, and may be occupied by an insulator, dielectric material, or air so that the two capacitive elements 155 act as a capacitor when supplied with power.

Inductive element 150 and capacitive element 155 may be shielded, jacketed, or insulated, and can connect to a power supply of wearable therapeutic device 100. This power supply can also be associated with defibrillator 115, controller 130, alarm module 120, or monitor 125. In one embodiment, wearable therapeutic device 100 can include both inductive element 150 and capacitive element 155.

Inductive element 150 and capacitive element 155 can stretch or expand together with garment 105. For example, inductive element 150 can include wire configured in a serpentine pattern or a wire configured in a coiled pattern whose radius and the number of turns or coils over a defined length change when stretched, which changes the inductance of inductive element 150. When capacitive element 155 is stretched together with garment 105, the capacitance changes, for example reducing when stretched. In one embodiment, controller 130 detects the inductance of inductive element 150 or capacitance of capacitive elements 155 to determine if sensing electrode 135 or therapy electrode 140 is properly or improperly positioned. For example, inductance or capacitance outside of a tolerance range or above or below a threshold value can indicate that sensing electrode 135 or therapy electrode 140 is improperly positioned or tensioned due to garment 105 stretching, and inductance or capacitance within a tolerance range or above or below a threshold value can indicate that no or minimal stretching of garment 105 has occurred and that electrodes 135 and 140 are properly positioned about the subject.

In one embodiment, sensing electrodes 135 or therapy electrodes 140 are properly positioned when they are adequately pressured by garment 105 to be firmly pressed against the subject so that they are held in a substantially fixed position to sense the subject's condition or deliver treatment. Properly positioned sensing electrodes 135 and therapy electrodes 140 are generally held by garment 105 in a fixed position with minimal movement and in contact the subject's skin. Conductive fluid or other materials may be present between sensing electrodes 135 or therapy electrodes 140 and the subject's skin.

Alarm module 120, which may include an interface and be part of monitor 125, can indicate both proper and improper positioning of electrodes 135 and 140, and can instruct the user to take corrective action, for example when the determined inductance of inductive element 150 or capacitance of capacitive element 155 indicates that stretching of garment 105 has displaced electrodes 135 or 140 so they are improperly positioned.

Figure 2:
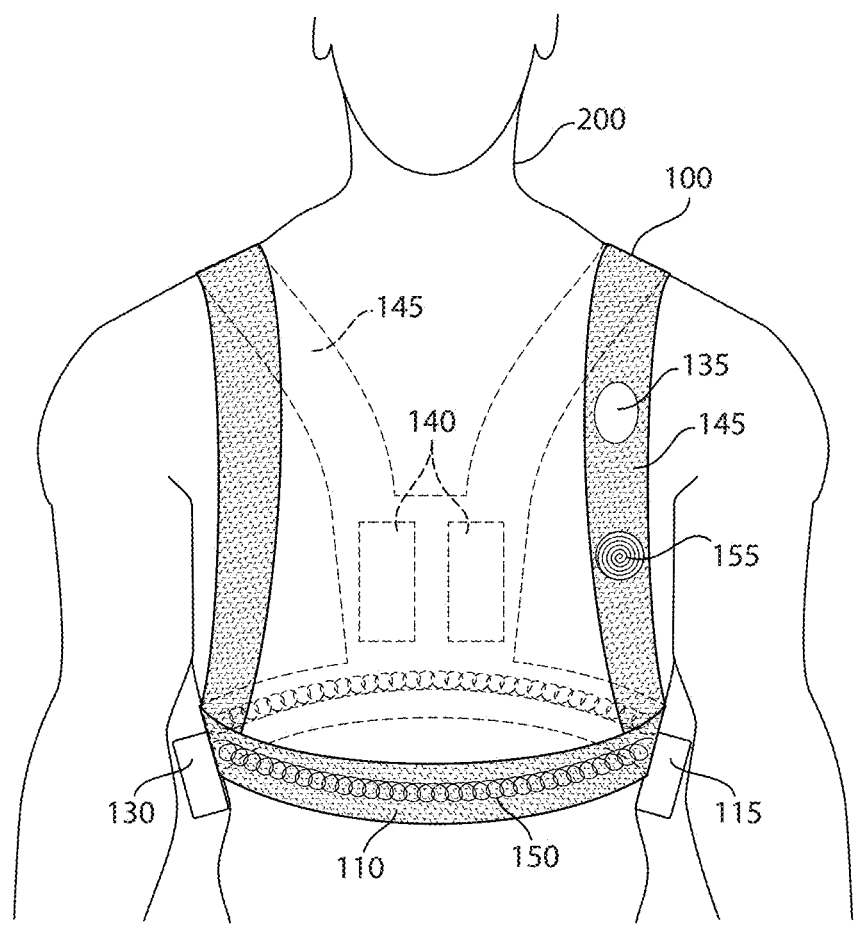
FIG. 2 is a schematic diagram depicting a wearable therapeutic device in accordance with an embodiment.

FIG. 2 is a schematic diagram depicting subject 200 wearing wearable therapeutic device 100 in accordance with an embodiment. In the example of FIG. 2, inductive element 150 is included in belt 110 and extends circumferentially around subject 200, and capacitive element 155 is included in strap 145 in a tightly wrapped pattern configured to stretch with strap 145. Other configurations are possible. For example, inductive element 150 can be included in strap 145 and capacitive element 155 can be included in belt 110. Further, inductive element 150 and capacitive element 155 can extend across or be disposed in any portion of garment 105, and need not be circumferential as illustrated in FIG. 2.

Wearable therapeutic device 100 can also include more than one inductive element 150 and more than one capacitive element 155, and need not include both types of elements. For example, a first inductive element 150 or capacitive element 155 can be included in a portion of belt 110 and a second inductive element 150 or capacitive element 155 can be included in a portion of strap 145 on one side of the subject, without extending around the subject. In one embodiment, a single inductive element 150 or capacitive element 155 is included in portions of both belt 110 and strap 145. Wearable therapeutic device 100 can include other elements not illustrated in FIG. 2, such as additional straps across the chest of subject 200 that can include inductive element 150 or capacitive element 155.

In one embodiment, controller 130 determines the inductance of inductive element 150, or the capacitance of capacitive element 155. Based on the determined inductance or capacitance, controller 130 can instruct alarm module 120 to provide a notification to subject 200. The notification can instruct subject 200 to loosen or tighten at least a portion of garment 105 (e.g., belt 110). The notification can also indicate that an arrhythmic cardiac event has been detected, based on information from sensing electrode 135.

FIG. 3A depicts a portion of wearable therapeutic device 100 that includes inductive element 150 in an unstretched position, and FIG. 4A depicts a portion of wearable therapeutic device 100 that includes inductive element 150 in a stretched position. In one embodiment, controller 130 can determine differences between the inductance of inductive element 150 in the unstretched position of FIG. 3A and the stretched position of FIG. 4A. For example, wearable therapeutic device 100 may have the unstretched configuration of FIG. 3A when it is not being worn by the subject, or if it is too large for the subject; and may have the stretched configuration of FIG. 4A if it is too small for the subject or is currently being worn by the subject.

FIG. 3B depicts a portion of wearable therapeutic device 100 that includes capacitive elements 155 in an unstretched position, and FIG. 4B depicts a portion of wearable therapeutic device 100 that includes capacitive elements 155 in a stretched position. An insulator, space, gap, or dielectric 160 may be present between the two capacitive elements 155. In one embodiment, controller 130 can determine differences between the capacitance of capacitive element 155 in the unstretched position of FIG. 3B and the stretched position of FIG. 4B, as stretching or movement of garment 105 changes the relative capacitive surface area and/or distance between capacitive elements 155. Electrodes 135 and 140 can be either properly or improperly positioned about the subject in the configurations of FIGS. 3A, 3B, 4A, and 4B. It should be appreciated that inductive element 150 may alternatively have a serpentine shape as shown in FIGS. 3B and 4B instead of the coiled shape shown in FIGS. 3A and 4A.

Inductive element 150 and capacitive element 155 can include a wire or thread sewn into garment 105. In one embodiment, inductive element 150 or capacitive elements 155 can expand and contract with garment 105, but otherwise substantially maintain their shape. Inductive element 150 and can also be wrapped around a core included in belt 110, strap 145, or other portion of garment 105.

Figure 5:
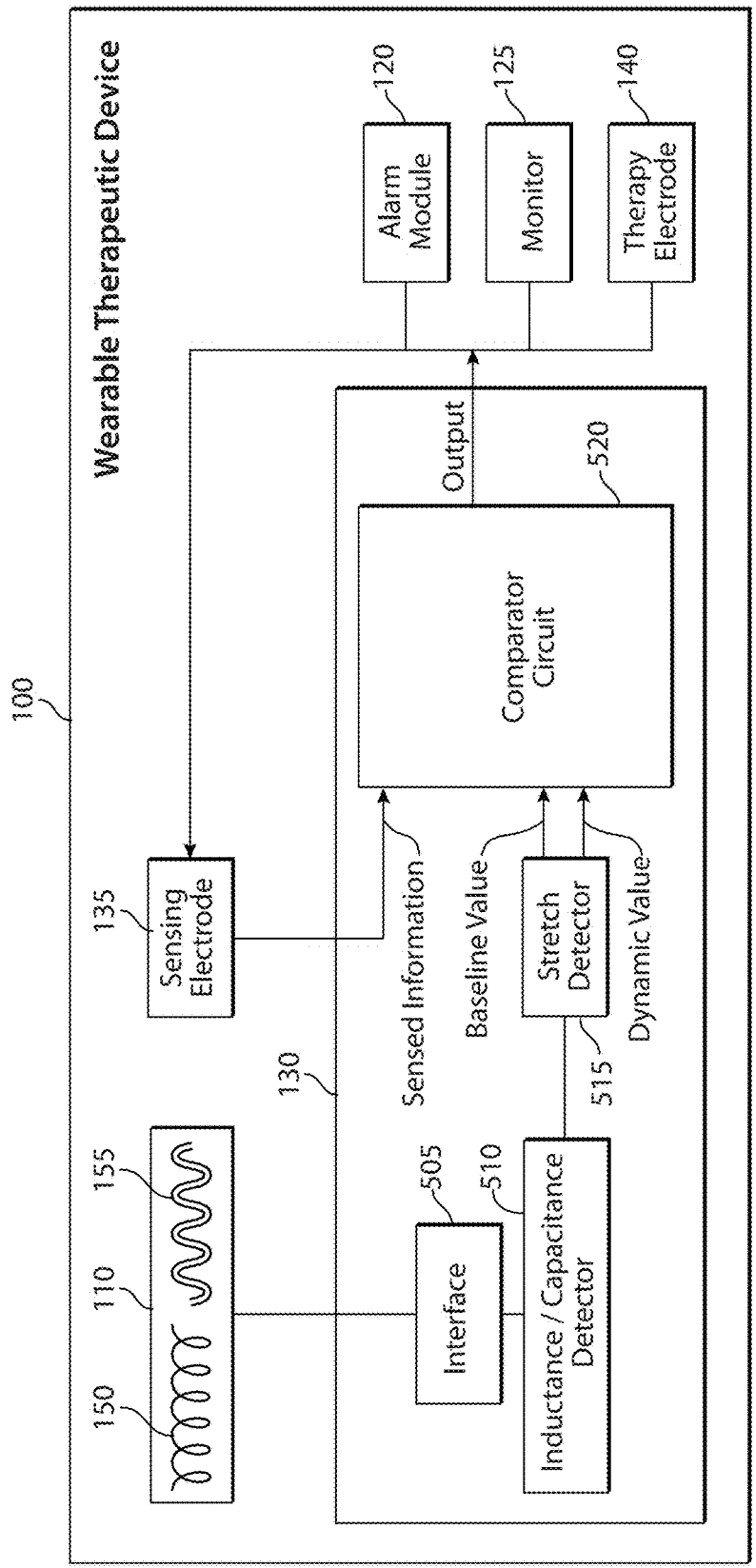
FIG. 5 is a functional block diagram depicting a wearable therapeutic device controller in accordance with an embodiment.

FIG. 5 depicts an example configuration of controller 130. In one embodiment, interface 505 connects inductive element 150 or capacitive element 155 with detector 510 (e.g. a logic device or circuit) to measure the inductance of inductive element 150 or the capacitance of capacitive element 155. Stretch detector 515 determines if at least a portion of garment 105 has stretched based upon the measured inductance or capacitance value. For example, controller 130 can determine the inductance or capacitance with garment 105 in an unstretched position at a baseline first time when wearable therapeutic device 100 is not being worn; and in a stretched position at a second time when wearable therapeutic device 100 is being worn. In one embodiment, comparator circuit 520 compares the unstretched baseline inductance or capacitance value with the stretched inductance or capacitance value to determine whether or not garment 105 has expanded or stretched, or to determine relative stretching between the baseline and stretched values. Based on this comparison, controller 130 and alarm module 120 can alert the subject to a number of conditions, such as garment 105 being too loose or too tight, that garment 105 is appropriately snug against the body of the subject, or that garment 105 is soiled and needs to be laundered to restore its elasticity, or that the garment should be replaced for example, due to its age.

Figure 6:
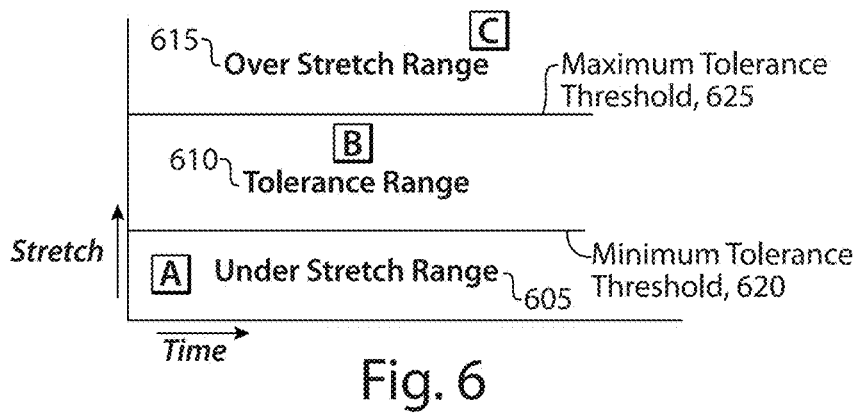
FIG. 6 is a graph depicting tolerance stretch ranges of a wearable therapeutic device in accordance with an embodiment.

FIG. 6 is a graph depicting tolerance stretch ranges of wearable therapeutic device 100 in accordance with an embodiment. In the example of FIG. 6, when worn by subject 200, wearable therapeutic device 100 can be classified in under stretch range 605, tolerance range 610, or over stretch range 615. These classifications can change with time, and subject 200 can adjust wearable therapeutic device 100 components such as belt 110 to change the classification between these ranges.

Wearable therapeutic device 100 can be determined by controller 130 to be in or under stretch range 605, (e.g., Point A), tolerance range 610 (e.g., Point B), or over stretch range 615 (e.g., Point C). Under stretch range 605 can indicate that wearable therapeutic device 100 is too loose or not sufficiently expanded, so that sensing electrode 135 or therapy electrode 140 is not in a substantially fixed position, or is not tightly fitted against subject 200. When controller 130 determines that wearable therapeutic device 100 is in under stretch range 605 based on the inductance of inductive element 150 or the capacitance of capacitive element 155, alarm module 120 can instruct subject 200 to take some action, such as to tighten belt 110 or straps 145, to launder garment 105 to improve its elasticity, or to replace garment 105 with a new one or one of a smaller size. For example, when the amount of stretching deteriorates from a baseline value over time, garment 105 may be losing elasticity and can be laundered to reintroduce elasticity to make garment 105 tighter fitting. When stretching deteriorates too rapidly between launderings from a baseline value, e.g., is below minimum tolerance threshold 620 and is too loose, garment 105 may be nearing end of life and be in need of replacement. When controller 130 determines that wearable therapeutic device 100 is over expanded or in over stretch range 615, alarm module can instruct subject 200 to loosen belt 110 or straps 145, or to replace garment 105 with a new one or one of a larger size. In one embodiment, controller 130 prevents application of treatment from therapy electrode 140 when garment 105 is determined to be in under stretch range 605 and/or over stretch range 615. Controller 130 can also disregard or give less weight to information received from sensing electrode 135 when garment 105 is determined to be in under stretch range 605 or over stretch range 615 because these positions outside tolerance range 610 can indicate that sensing electrode 135 is not properly positioned about subject 200.

In one embodiment, controller 130 can determine that garment 105 is within tolerance range 610 and thus properly fitted about subject 200 with sensing electrode 135 or therapy electrode 140 properly and snugly positioned with respect to subject 200. When controller 130 determines or verifies that wearable therapeutic device 100 is within tolerance range 610, controller 130 can evaluate information received from sensing electrode 135 to determine that subject 200 is or is not in need of therapy to treat, for example, an abnormal cardiac or respiratory event. Continuing with this example, controller 130 can direct therapy electrode 140 and defibrillator 115 to apply treatment to subject 200.

In one embodiment, minimum tolerance threshold 620 and maximum tolerance threshold 625 are the limits of tolerance range 610. Thresholds 620 and 625 need not be linear as depicted in FIG. 6. In one embodiment, thresholds 620, 625 can change with time. For example, as wearable therapeutic device 100 degrades or becomes worn with time, minimum tolerance threshold 620 can increase, indicating an increase in tightening may be necessary to position sensing electrode 135 or therapy electrode 140. Alternatively, where a significant amount of noise on sensing electrode 135 is detected at a particular stretch level, or where a number of fall-off flags have been detected, or both; controller 130 may adjust the minimum tolerance threshold to this level of stretch. In this example, controller 130 includes auto-learn or adaptive features where controller 130 adjusts tolerance thresholds 620 or 625, or tolerance range 610, based on sensed electrode positioning, electrode fall off events, the force applied by garment 105 onto the subject, or feedback from the subject regarding observed conditions or the subject's comfort level. Maximum tolerance threshold 625 can also increase over time, as for example subject 200 becomes accustomed to wearable therapeutic device 100 and is able to comfortably withstand a tighter fit. In one embodiment, garment 105 exerts 0.050 lb of force on the subject's body at minimum tolerance threshold 620 and 1.70 lb of force on the subject's body at maximum tolerance threshold 625.

The auto-learn features of controller 130 can associate a particular fitting or level of snugness of garment 105 about subject 200 with a substantially noise or artifact free ECG signal measured by sensing electrode 135. For example, controller 130 can identify an amount of force exerted by garment 105 on subject 200 during sensing of a usable ECG signal by sensing electrode 135. In this example, the amount of force identified by controller 130 is based on the detected inductance of inductive element 150 or the detected capacitance of capacitive element 155. Controller 130 in this example identifies a tolerance range 610 that includes this detected amount of force. If controller 130 detects that garment 105 is in under stretch range 605 (e.g., too loose) or over stretch range 615 (e.g., too tight), controller 130 can instruct subject 200 to tighten or loosen garment 105, for example via alarm module 120 or monitor 125, to bring the force level within that of tolerance range 610. In this example, controller 130 identifies and continuously adjusts a custom tolerance range 610 for an individual subject 200 and a particular garment 105 based on the fit of that garment 105 that provides sufficient force for a substantially artifact free ECG signal.

Thus, with the auto-learn feature, controller 130 can determine or adjust the range of tolerance range 610 based on the quality of ECG signals sensed by sensing electrode 135. For example, the force exerted by garment 105 on subject 200 during sensing of a substantially noise or artifact free ECG can be evaluated by controller 130 to determine the scope of tolerance range 610, with the force associated with a quality ECG signal being within tolerance range 610. Controller 130 can adjust this range with time, for example as subject 200 gains or loses weight, or as garment 105 wears and its elasticity characteristics change. It should be appreciated that the level of snugness associated with a quality ECG signal, and thus tolerance range 610, may vary from subject to subject.

In one embodiment, when wearable therapeutic device is in tolerance range 610, garment 105 has an acceptable range of stretching. In this illustrative embodiment, controller 130 can determine that sensing electrode 135 and therapy electrode 140 are in proper position about subject 200. Based on changes in the inductance or capacitance caused by garment 105 expansion, controller 130 can determine respiration information (e.g., rates and volumes) of subject 200. Sensing electrode 135, which may include an accelerometer, can also sense this information. Respiratory information can also be determined based on the inductance or capacitance, which may change as garment 105 expands or contracts with respiration. In one embodiment, controller 130 evaluates respiration information and electrocardiogram information to detect an arrhythmia.

Ranges 605, 610, and 615, and thresholds 620 and 625 can be indicated as stretching distances of garment 105, belt 110, strap 145 or other components, as well as changes in circumference, diameter, or radius of these components. These ranges and thresholds can be determined based on inductance values of inductive element 150 or on the capacitance values of capacitive element 155. They can be indicated with inductance values, capacitance values, or units of distance.

In one embodiment, controller 130 evaluates the inductance or capacitance and determines that garment 105 stretching is within tolerance range 610. In this example, sensing electrodes 135 sense cardiac (e.g., electrocardiogram) information about subject 200. Respiratory information can also be sensed or deduced from changes in inductance or capacitance. In this example, the cardiac information can indicate that subject 200 is suffering an arrhythmia at the same time the respiratory information indicates that subject 200 has stopped breathing. Because, in this example, garment 105 is within tolerance range 610, controller 130 can determine with a high level of confidence that sensing electrodes 135 are properly positioned. Based on this confidence level and the sensed information, controller 130 can determine that the sensed information is accurate and that subject 200 is experiencing an arrhythmia and in need of treatment. With garment 105 within tolerance range 610, controller 130 can also determine with a high level of confidence that therapy electrode 140 is properly positioned to apply an electric shock to subject 200 to treat the arrhythmia. In one embodiment, where an arrhythmia has been detected but controller 130 determines garment 105 is within tolerance range 610 and respiratory information indicates normal breathing, controller 130 may reduce the confidence level that the arrhythmia has been detected and/or that the subject is in need of treatment.

Controller 130 can also determine that garment 105 is stretched outside of tolerance range 610, (e.g., over or under stretched). In this example, respiration and cardiac information may be inconsistent with each other due to movement or improper positioning with respect to subject 200. Noise artifacts can further interfere with the sensed information. Continuing with this example, controller 130 can have a low level of confidence that sensing electrodes 135 are properly positioned, (or a high level of confidence that they are improperly positioned). Based on this confidence level and the sensed information, controller 130 can determine that the sensed information is inaccurate because the sensor is improperly positioned, and that subject 200 is not experiencing an arrhythmia and does not need treatment. In this example, controller 130 can withhold, prevent, or block treatment from therapy electrode 140 to subject 200 until controller 130 determines with sufficient confidence that information from sensing electrodes 135 is reliable and that sensing electrodes 135 and therapy electrode 140 are properly positioned. Further, controller 130 can adjust the behavior of wearable therapeutic device 100 based on the confidence level. For example, where the confidence level is low or decreasing with respect to a previous confidence level, controller 130 (and sensing electrodes 135) can sense ECG signals more frequently, or controller 130 can lengthen a response time during which the subject can respond to an alarm indicating a detected arrhythmia, or both.

Wearable therapeutic device 100 can identify arrhythmic cardiac events and apply treatment when garment 105 is in any range, including under stretch range 605, tolerance range 610, and over stretch range 615. For example, while in tolerance range 610, controller 130 can identify an arrhythmia with less sensed information due to a high confidence level that the sensed information is accurate, and can direct therapy electrodes 140 to apply treatment due to a high confidence level that they are properly positioned. While in ranges 605 or 615, controller 130 may have a lower confidence level that the sensed information is accurate and that electrodes 135, 140 are properly positioned. In this example, controller 130 may compensate for possible artifacts or flaws in the sensed information by evaluating sensed information over a longer period of time, or by evaluating information provided by additional sensors 135 to identify an arrhythmia. Via alarm module, controller 130 may prompt subject 200 for a response or ask the subject to indicate distress, where an affirmative response or lack of any response indicates that the subject is in need of treatment. In one embodiment, controller 130 may direct therapy electrode 140 to apply treatment even when therapy electrode 140 is improperly positioned. The applied treatment may still be effective even though there may be a higher impedance between therapy electrodes 140 and the subject's skin in this example.

In one embodiment, controller 130 determines different degrees of confidence that the sensed information is accurate and that electrodes 135 and 140 are properly positioned. There can be two possible confidence levels (e.g., high/low, zero/one, yes/no) or confidence levels can be provided as percentages (e.g., a 60% chance that the sensed information is accurate). Based on the confidence level, controller 130 can evaluate more or less sensed information, from sensing electrode 135, inductive element 150, or capacitive element 155 to provide a notification to the subject regarding positioning of wearable therapeutic device 100, detection of an arrhythmia, or application of treatment. In one embodiment, suggestions or requirements are provided to subject 200 to increase the confidence level, such as suggesting that subject 200 tighten garment 105 if subject 200 can tolerate the tightening, or indicate that sensors 135 and 140 are non-functional due to improper positioning and require their tightening or replacement.

Figure 7:
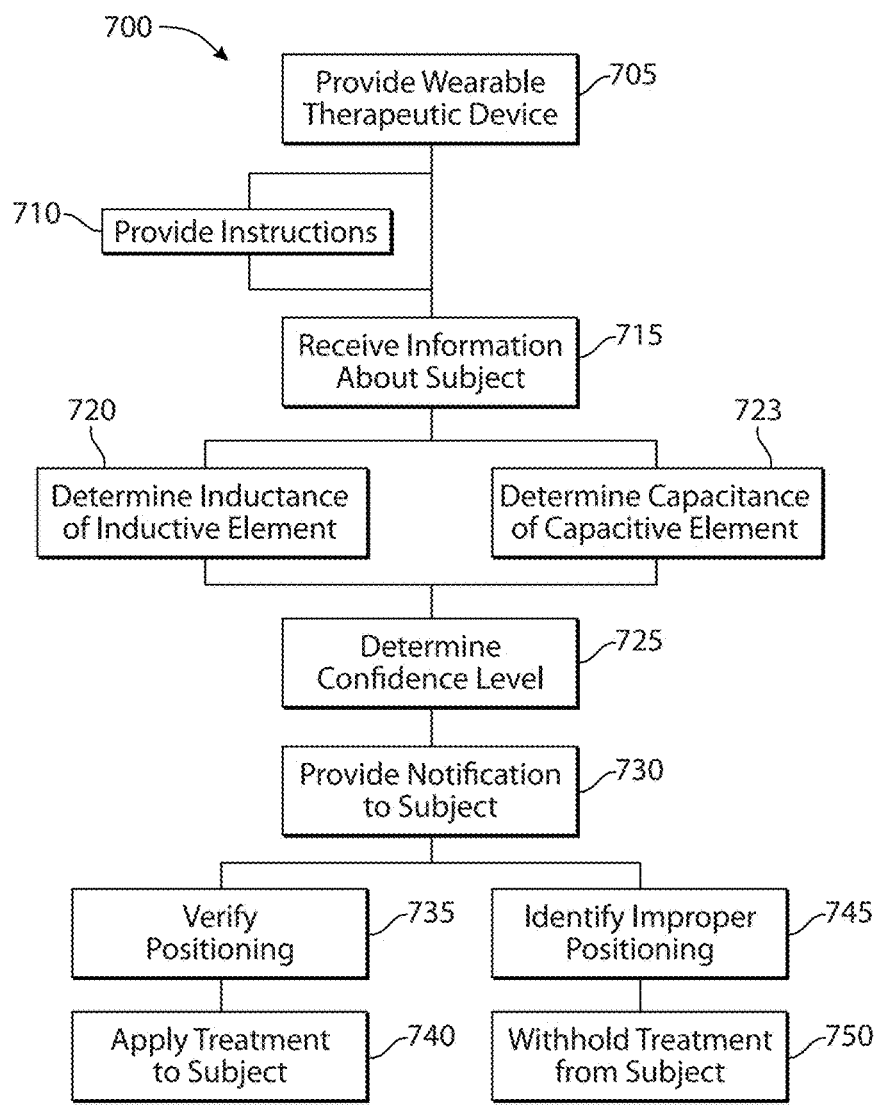
FIG. 7 is a flow chart depicting a method of facilitating care of a subject in accordance with an embodiment.

FIG. 7 is a flow chart depicting a method 700 of facilitating care of a subject. In one embodiment, method 700 includes an act of providing a wearable therapeutic device (ACT 705). In one embodiment, providing the wearable therapeutic device (ACT 705) includes providing a device that includes a sensing electrode. The sensing electrode may be housed in a garment of the wearable therapeutic device, and providing the wearable therapeutic device (ACT 705) may include providing a device with an inductive element or capacitive element included in at least part of the garment. Providing the wearable therapeutic device (ACT 705) may also include providing a device having a controller configured to determine inductance of the inductive element or capacitance of the capacitive element, and to determine, based on the determined inductance or capacitance, a confidence level of information received from the sensing electrode. This information may include electrocardiograph or other information about the subject's body functions. Providing the wearable therapeutic device (ACT 705) may also include providing a device with an alarm module coupled with a controller to notify the subject of events, conditions, or information about the subject's condition or about the condition of the wearable therapeutic device, based on the confidence level of the information received from the sensor and the determined inductance of the inductive element.

In one embodiment, method 700 includes an act of providing instructions (ACT 710). For example, providing instructions (ACT 710) can include providing instructions to operate the wearable therapeutic device, or providing instructions on how to wear the wearable therapeutic device. In one embodiment, the instructions include instructions to the subject regarding positioning of wearable therapeutic device components, such as sensing or therapy electrodes. For example, instructions can be provided (ACT 710) to the subject, based on an expansion of the wearable therapeutic device or its components, to position an electrode proximate to an area of the subject's body, such as the center of the back, or proximate to the chest and heart of the subject, so that the electrodes are positioned to provide therapy to the subject or sense cardiac or respiratory function of the subject.

In one embodiment, method 700 includes an act of receiving information about the subject (ACT 715). In one embodiment, this information is received (ACT 715) from at least one sensing electrode. For example, receiving information (ACT 715) may include receiving sensed electrocardiograph information of the subject. In this example, the received information includes information from a sensing electrode that is part of the wearable therapeutic device and that can detect electrocardiograph signals from a subject wearing the device. The received (ACT 715) information can include cardiac, pulse, circulatory, respiratory, or pulmonary information of the subject. In one embodiment, receiving information (ACT 715) includes receiving information about the inductance of an inductive element or capacitance of a capacitive element disposed in part of the wearable therapeutic device. The inductance value, capacitance value or changes in these values with time can indicate that the wearable therapeutic device is in a stretched, expanded, or unexpanded position.

Method 700 also includes an act of determining inductance of an inductive element included in the wearable therapeutic device (ACT 720). In one embodiment, inductance is determined (ACT 720) with a sensor that is part of the wearable therapeutic device that measures the inductance, or a logic device associated with the controller calculates inductance based, for example, on the radius, number of turns, or length of the coils of the inductive element disposed in the wearable therapeutic device.

Method 700 alternatively or additionally includes an act of determining capacitance of a capacitive element included in the wearable therapeutic device (ACT 723). In one embodiment, capacitance is determined (ACT 723) with a sensor that is part of the wearable therapeutic device that measures the capacitance, or a logic device associated with the controller calculates capacitance of the capacitive element.

In one embodiment, method 700 includes an act of determining a confidence level (ACT 725) of the received (ACT 715) information about the subject. The confidence level may be determined (ACT 725) based on changes in the inductance or capacitance with respect to a baseline or threshold value. In one embodiment, the confidence level is determined based on identified expansion or stretching of a portion of the wearable therapeutic device or any of its components. For example, the confidence level can be determined based on the expansion of the inductive element or capacitive element, a belt or other portion of the wearable therapeutic device that includes either of these elements, or a circumference of the wearable therapeutic device, its belt, strap, or garment. In one embodiment, the confidence level is determined based on an expansion of a portion of the wearable therapeutic device that includes the inductive element or capacitive element and received information (ACT 715) about the subject that includes electrocardiograph information.

Determining the confidence level (ACT 725) may include determining that the received information about the subject is accurate. For example, the determined inductance (ACT 720) or capacitance (ACT 723) can indicate that the wearable therapeutic device has not stretched, or has stretched less than a threshold amount, or within a defined acceptable parameter or range. In this example, the confidence level of the accuracy of the sensed information about the subject can be determined (ACT 725) to be high, e.g., the sensed electrocardiograph or other information about the subject can be accepted as valid information about the subject's health and used as a factor in diagnosing the subject, e.g., by identifying an arrhythmic cardiac event, or applying treatment to the subject.

Determining the confidence level (ACT 725) may include determining that the received information about the subject is not accurate. In this example, the determined inductance (ACT 720) or capacitance (ACT 723) can indicate that the wearable therapeutic device has stretched to a degree that the sensing electrode that senses the received (ACT 715) information about the subject may have shifted about the subject to a degree where it is no longer properly positioned to sense, for example, a quality electrocardiogram signal. In this example, the confidence level in the accuracy of the sensed information can be low, and the sensed information may be disregarded or require further verification.

In one embodiment, method 700 includes an act of providing a notification to the subject (ACT 730) based on the confidence level. The notification may be audibly, visually, or haptically (e.g., a vibrating alarm) provided (ACT 730) to the subject. The notification may also be provided (ACT 730) to another person such as the subject's doctor, family member, friend, or health care provider, who may be proximate to the subject or at a remote location, e.g., via a transmission over a network. In one embodiment, the notification is provided to the subject (ACT 730) by an alarm module, monitor, or interface that is part of the wearable therapeutic device.

Providing the notification (ACT 730) may include providing a diagnosis of an arrhythmic cardiac event, fibrillation, cardiac arrest, abnormal respiratory activity, or other condition that may require medical attention. The provided notification (ACT 730) can indicate that the subject has no immediate health issue requiring treatment, e.g., a normal cardiac rhythm or normal pulmonary activity. Providing the notification (ACT 730) can also include providing information unrelated to the subject's health, such as information about the use or positioning of the wearable therapeutic device. For example, information can be provided (ACT 730) indicating that the sensing or therapy electrodes of the wearable therapeutic device are not properly positioned with respect to the subject wearing the device. This may be due to stretching of the wearable therapeutic device with time and use. This stretching can cause the electrodes to shift position to a location where they are less effective or ineffective to sense information about the subject or apply treatment to the subject.

In one embodiment, method 700 includes an act of verifying positioning of wearable therapeutic device components (ACT 735), such as sensing or therapy electrodes. For example, the position of wearable therapeutic device components can be verified (ACT 735) when the identified inductance (ACT 720) or capacitance (ACT 723) is analyzed to determine that the amount of stretching of the wearable therapeutic device is less than a threshold amount, or within a tolerance range. This minimal stretching can indicate a tolerable level of displacement of wearable therapeutic device components. Method 700 may also include an act of applying treatment to the subject (ACT 740). In one embodiment, applying treatment to the subject (ACT 740) includes delivering an electric shock to the subject from therapy electrodes that are included in the wearable therapeutic device and an associated defibrillator.

Method 700 can also include an act of identifying improper positioning of wearable therapeutic device components (ACT 745). For example, improper positioning of wearable therapeutic device components can be identified (ACT 745) when the identified inductance (ACT 720) or capacitance (ACT 723) is analyzed to determine that the amount of stretching of the wearable therapeutic device is more than a threshold amount, or outside a tolerance range. This stretching can indicate an unacceptable level of displacement of wearable therapeutic device components during use of the wearable therapeutic device. Method 700 may also include an act of withholding treatment from the subject (ACT 750). In one embodiment, withholding treatment from the subject (ACT 740) includes delaying delivery an electric shock to the subject from therapy electrodes that are included in the wearable therapeutic device and an associated defibrillator until the therapy electrodes are moved to an appropriate location proximate to the subject, and until their positioning is verified (ACT 735). Withholding treatment from the subject (ACT 750) can also include delaying delivery of an electric shock to the subject until sensing electrodes are moved to an appropriate location proximate the subject so that they can sense information at a confidence level sufficient to rely on for diagnosing the subject's condition.

Having now described some illustrative embodiments, it is apparent that the foregoing is illustrative and not limiting, having been presented by way of example.

In particular, although many of the examples presented herein involve specific combinations of method acts or system elements, it is understood that those acts and those elements may be combined in other ways. Acts, elements and features discussed only in connection with one embodiment are not intended to be excluded from a similar role in other embodiments.

Note that in FIGS. 1 through 7, the enumerated items are shown as individual elements. In actual implementations of the systems and methods described herein, however, they may be inseparable components of other electronic devices such as a digital computer. Thus, actions described above may be implemented at least in part in software that may be embodied in an article of manufacture that includes a program storage medium. The software may be executed by a processor of controller 130. In one embodiment, the program storage medium is non-transient. The program storage medium includes data signals embodied in one or more of a carrier wave, a computer disk (magnetic, or optical (e.g., CD or DVD, or both)), non-volatile memory, tape, a system memory, and a computer hard drive.

Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements to single or plural configurations. References to any act or element being based on any information, act or element may include embodiments where the act or element is based at least in part on any information, act, or element.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment in any manner consistent with the aspects and embodiments disclosed herein.

References to "or" should be construed as inclusive so that any terms described using "or" may indicate any of a single, more than one, and all of the described terms. Intervening embodiments, acts, or elements are not essential unless recited as such.

Where technical features in the drawings, detailed description or any claim are followed by reference signs, the reference signs have been included for the sole purpose of increasing the intelligibility of the drawings, detailed description, and claims. Accordingly, neither the reference signs nor their absence have any limiting effect on the scope of any claim elements.

One skilled in the art will realize the systems and methods described herein may be embodied in other specific forms without departing from the characteristics thereof. For example, the subject may be a patient and the wearable therapeutic device can store and transmit data concerning the patient's medical condition to a physician. Because the wearable therapeutic device can operate essentially at all times, this data can be used to generate a comprehensive real time record of the subject's health over an extended period of time. The foregoing embodiments are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A wearable medical device, comprising:
a garment worn by a subject, the garment comprising one or more electrocardiograph sensing electrodes configured to receive electrocardiograph information from the subject;
at least one of an inductive element and a capacitive element included in at least part of the garment; and
a controller configured to determine a confidence level of the electrocardiograph information received from the one or more electrocardiograph sensing electrodes based on at least one of a change in an inductance of the inductive element and a change in a capacitance of the capacitive element, the confidence level indicating whether the one or more electrocardiograph sensing electrodes are properly positioned on the subject.

2. The wearable medical device of claim 1, further comprising an alarm module coupled to the controller and configured to provide a notification to the subject based on the confidence level.

3. The wearable medical device of claim 2, wherein the notification indicates that the garment is one of: properly positioned about the subject, too loose about the subject, and too tight about the subject.

4. The wearable medical device of claim 1, wherein the controller is further configured to identify, based on the at least one of the change in the inductance of the inductive element and the change in the capacitance of the capacitive element, at least one of: expansion of the garment, tightening of the garment, improper positioning of the garment, and shifting of the garment.

5. The wearable medical device of claim 4, further comprising a therapy electrode included in the garment and wherein the controller is further configured to determine, based on the at least one of the expansion of the garment, the tightening of the garment, the improper positioning of the garment, and the shifting of the garment, that positioning of at least one of the one or more electrocardiograph sensing electrodes and the therapy electrode is outside a tolerance range and to withhold treatment of the subject by the therapy electrode based on the positioning of the at least one of the one or more electrocardiograph sensing electrodes and the therapy electrode.

6. The wearable medical device of claim 5, further comprising an alarm module configured to provide instructions to the subject regarding positioning of at least one of the one or more electrocardiograph sensing electrodes and the therapy electrode based on the at least one of: the expansion of the garment, the tightening of the garment, the improper positioning of the garment, and the shifting of the garment.

7. The wearable medical device of claim 1, wherein the controller is further configured to identify an expansion of the garment based on the at least one of the change in the inductance of the inductive element and the change in the capacitance of the capacitive element and to determine respiratory function of the subject based on the expansion of the garment.

8. The wearable medical device of claim 1, further comprising a therapy electrode included in the garment, wherein the confidence level further indicates whether the therapy electrode is properly positioned on the subject, and wherein the controller is further configured to identify an arrhythmic cardiac event, verify positioning of the therapy electrode included in the garment based on the confidence level, and cause the therapy electrode to apply treatment to the subject.

9. The wearable medical device of claim 1, wherein the garment comprises at least one of a belt and a strap configured to include the at least one of the capacitive element and the inductive element, and at least one of: the one or more electrocardiograph sensing electrodes, the controller, an alarm module, a therapy electrode, and a defibrillator.

10. The wearable medical device of claim 1, wherein the wearable medical device includes both the inductive element and the capacitive element, and wherein the controller is configured to determine the confidence level of information received from the one or more electrocardiograph sensing electrodes based on both the change in the inductance of the inductive element and the capacitance of the capacitive element.

11. The wearable medical device of claim 1, wherein the controller is further configured to determine the confidence level at least in part by determining that the one or more electrocardiograph sensing electrodes is properly positioned on the subject based on the at least one of the change in the inductance of the inductive element and the change in the capacitance of the capacitive element.

12. The wearable medical device of claim 1, wherein the one or more electrocardiograph sensing electrodes senses electrocardiograph information of the subject, and wherein the controller is further configured to determine the confidence level based on the electrocardiograph information of the subject and the at least one of the change in the inductance of the inductive element and the change in the capacitance of the capacitive element.

13. The wearable medical device of claim 1, wherein the controller is further configured to determine an absence of an arrhythmic cardiac event based on the electrocardiograph information of the subject and the at least one of the change in the inductance of the inductive element and the change in the capacitance of the capacitive element.

14. The wearable medical device of claim 1, wherein the wearable medical device is a wearable therapeutic device.

* * * * *

UNITED STATES PATENT AND TRADEMARK OFFICE
CERTIFICATE OF CORRECTION

PATENT NO. : 9,848,826 B2
APPLICATION NO. : 14/630920
DATED : December 26, 2017
INVENTOR(S) : Shane S. Volpe et al.

Page 1 of 1

It is certified that error appears in the above-identified patent and that said Letters Patent is hereby corrected as shown below:

In the Claims

Column 20, Line 33, Claim 10, insert -- change in the -- between "the" and "capacitance".

Signed and Sealed this
Thirteenth Day of March, 2018

Andrei Iancu
*Director of the United States Patent and Trademark Office*